United States Patent [19]

Iizuka et al.

[11] Patent Number: 4,870,183

[45] Date of Patent: Sep. 26, 1989

[54] NOVEL AMINO ACID DERIVATIVES

[75] Inventors: Kinji Iizuka; Tetsuhide Kamijo; Tetsuhiro Kubota; Kenji Akahane, all of Nagano; Hideaki Umeyama, Chiba; Yoshiaki Kiso, Osaka, all of Japan

[73] Assignee: Kissei Pharmaceutical Co., Ltd., Nagano, Japan

[21] Appl. No.: 267,612

[22] Filed: Nov. 2, 1988

Related U.S. Application Data

[63] Continuation of Ser. No. 71,822, Jul. 10, 1987, abandoned.

[30] Foreign Application Priority Data

Jul. 11, 1986 [JP] Japan ................... 61-164254

[51] Int. Cl.$^4$ ............... C07D 401/00; C07D 233/64; C07K 5/08; C07K 5/06
[52] U.S. Cl. ................................. 546/210; 548/344; 530/331
[58] Field of Search ................. 546/210; 548/344; 530/331

[56] References Cited

U.S. PATENT DOCUMENTS

| | | | |
|---|---|---|---|
| 4,234,571 | 11/1980 | Nestor et al. | 424/177 |
| 4,548,926 | 10/1985 | Matsueda et al. | 514/19 |
| 4,591,648 | 5/1986 | Jones et al. | 548/344 |
| 4,595,677 | 6/1986 | Riniker et al. | 514/17 |
| 4,656,269 | 4/1987 | Iizuka et al. | 544/139 |
| 4,666,888 | 5/1987 | Raddatz et al. | 514/18 |
| 4,698,329 | 5/1987 | Matsueda et al. | 514/18 |
| 4,711,958 | 12/1987 | Iizuka et al. | |
| 4,814,342 | 3/1989 | Hoover et al. | 530/331 |

FOREIGN PATENT DOCUMENTS

| | | |
|---|---|---|
| 77028 | 4/1983 | European Pat. Off. . |
| 77029 | 4/1983 | European Pat. Off. . |
| 81783 | 6/1983 | European Pat. Off. . |
| 114993 | 8/1984 | European Pat. Off. . |
| 173481 | 3/1986 | European Pat. Off. . |
| 0229667 | 7/1987 | European Pat. Off. . |
| 0264106 | 4/1988 | European Pat. Off. . |
| 39149 | 8/1983 | Japan . |
| 103230 | 12/1984 | Japan . |
| 19100 | 8/1985 | Japan . |
| 201036 | 4/1986 | Japan . |
| 100595 | 5/1986 | Japan . |
| 137896 | 6/1986 | Japan . |
| 148167 | 7/1986 | Japan . |
| 273913 | 7/1986 | Japan . |
| 13908 | 12/1986 | Japan . |
| 265921 | 12/1986 | Japan . |
| 267947 | 12/1986 | Japan . |
| 285317 | 12/1986 | Japan . |
| 268415 | 6/1987 | Japan . |
| 18355188 | 7/1988 | Japan . |

OTHER PUBLICATIONS

Kobuku et al., "Highly Potent and Specific Inhibitors, Etc.," Biochemical and Biophysical Research Comm., vol. 118, No. 3, pp. 929-933 (2-1984).
106th Annual Meeting of Pharmaceutical Society of Japan (Apr. 1986)-Iizuka et al. presentation.
The 50th Annual Meeting of the Japanese Circulation Society (Mar. 1986)-Aoi et al., Abstract followed by presentation.
50th Annual Meeting of the Japanese Circulation Society (Mar. 1986) Miyazaki et al., abstr.
59th (general Meeting of the Japanese Pharmacological Society (Apr. 1986) Miyazaki et al., abstr. & presentation.
Brown et al., "Protection of histidine side-chains, etc." Chemical Abstracts 95:220299f (1981).
Colombo et al., "Acid-labile histidine side-chain protection," Chemical Abstracts 101:23914n (1984).
The Abstract of Miyazaki et al., presentation of the 9th Japanese Society of Hypertension.
The Abstract of the 8th Seminar of Antihypertension Drugs held on Apr. 2, 1987.
The Abstract of the American Society of Hypertension (ASH) World Biologically Active Artial Peptides (BAAP).
Abstract of Kubota et al., presentation at the 37th Regional Meeting of Japanese Pharmocological Society.
European Journal of Pharmacology vol. 129, No. 3, pp. 393-396, Toda et al. entitled "Human Renin Inhibiting dipeptide," 1986.

Primary Examiner—Delbert R. Phillips
Attorney, Agent, or Firm—Sughrue, Mion, Zinn, Macpeak & Seas

[57] ABSTRACT

Novel amino acid derivatives useful as a therapeutic agent are disclosed. These amino acid derivatives and the pharmaceutically acceptable salts thereof have a human renin inhibitory effect when administered orally and are useful for treatment of hypertension, especially renin-associated hypertension.

4 Claims, No Drawings

NOVEL AMINO ACID DERIVATIVES

This is a continuation of application Ser. No. 07/071,822, July 10, 1987 now abandoned.

FIELD OF THE INVENTION

This invention relates to novel amino acid derivatives useful as a therapeutic agent. More particularly, this invention relates to amino acid derivatives which have a human renin inhibitory effect when administered orally, and thus which are useful for treatment of hypertension, especially renin-associated hypertension.

BACKGROUND OF THE INVENTION

Renin is a proteolytic enzyme having a molecular weight of about 40,000, produced and secreted by juxtaglomerular cells in the kidney. This acts on the plasma renin substrate, angiotensinogen, to yield decapeptide angiotensin I which is converted into angiotensin II by an angiotensin I converting enzyme.

It is well known that angiotensin II contracts the vascular smooth muscle and acts on the adrenal cortex to secrete the aldosterone which regulates salts and water balance. Accordingly, the renin-angiotensin system plays an important role in hypertension. An effective inhibitor of renin has long been sought as an agent for treatment of hypertension, especially renin-associated hypertension. As a result, it has been found that certain peptides show a renin inhibitory effect, as described in U.S. Pat. No. 4,548,926, Japanese Patent Application (OPI) Nos. 163899/85, 275257/86, 78795/86, 227851/84, 155345/84, 110661/84, (The term "OPI" as used herein refers to an unexamined Japanese patent application); Japanese patent Publication No. 39149/83, Biochemical and Biophysical Research Communications, Vol. 118, pages 929–933, 1984; and European Patent Application Nos. 77029(A2), 77028(A2) and 81783(A2).

Of these prior art references, Japanese Patent Application (OPI) No. 163899/85 discloses peptides represented by the following formula:

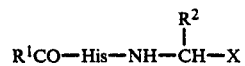

wherein
R$^1$CO represents an aliphatic acyl group, an aromatic acyl group, an aromatic aliphatic acyl group, a heterocyclic acyl group or a heterocyclic aliphatic acyl group, said acyl groups being able to have an amino group, a protected amino group, a hydroxy group, a substituted dithio group, an alkyl group, an alkoxy group, an alkoxycarbonyl group, a halogen atom or a nitro group as a substituent;
R$^2$ represents an isobutyl group or a sec-butyl group;
X represents a group of formula

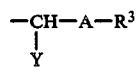

in which R$^3$ represents a carboxyl group, an N-substituted carbamoyl group, a carbazoyl group, an N-substituted carbazoyl group or an acyl group, A represents a single bond or an alkylene group, Y represents a hydroxy group, a mercapto group or a formyl group, or a group of formula

in which R$^4$ represents a substituted alkyl group having a carboxy group, a protected carboxy group, an N-substituted carbamoyl group, a carbazoyl group, an N-substituted carbazoyl group or an acyl group as a substituent;
His represents an L-histidyl group;
and pharmaceutically acceptable salts and esters thereof.

Japanese Patent Application (OPI) No. 78795/86 also discloses optical isomers of peptides disclosed in Japanese Patent Application (OPI) No. 163899/85.

Japanese Patent application (OPI) 275257/86 discloses peptides closely related to compounds of this invention. Although this reference does not specifically disclose, the compounds having following formula is included within the broad scope thereof:

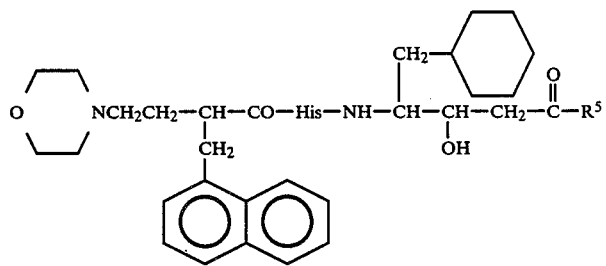

wherein R$^5$ represents an alkoxy group having 1 to 10 carbon atoms, a mono or di-alkylamino group having 1 to 10 carbon atoms or a heterocyclic group, said heterocyclic group being connected the carbonyl group in the formula with the nitrogen atom in said heterocyclic group, and pharmaceutically acceptable salts thereof.

However, this reference does not teach that compounds having a morpholinocarbonylmethyl group instead of the morpholinoethyl group exhibit an excellent renin inhibitory activity.

Furthermore, with regard to peptides related to those of this invention, the inventors of this invention also have filed some U.S. patent applications Ser. Nos. 789,597 (filed Oct. 21, 1985), 824341 (filed Jan. 31, 1986), 852,260 (filed Apr. 15, 1986), 879,741 (filed June 27, 1986), 903,803 (filed Sept. 14, 1986) and 32,693 (filed Apr. 1, 1987).

On the other hand, by someone of the present inventors and others, analogous peptides to those of this invention have been published in European Journal of Pharmacology, Vol. 129, No. 3, 393–396, 1986, and have been reported in the 50th Annual Scientific Meeting of the Japanese Circulation Society, March, 1986; the 59th General Meeting of the Japanese Pharmacological Society, April, 1986; the 106th Annual Meeting of Pharmaceutical Society of Japan, April, 1986; the 37th Regional Meeting (Kita area) of the Japanese Pharmacological Society, August, 1986; the 2nd annual meeting of the American Society of Hypertension, May, 1987.

SUMMARY OF THE INVENTION

An object of this invention is to provide new amino acid derivatives which exhibit a specific inhibitory effect on renin when administered orally to mammalia including humans.

Another object of this invention is to provide new amino acid derivatives and pharmaceutically acceptable salts thereof.

A further object of this invention is to provide pharmaceutical compositions comprising new amino acid derivatives or pharmaceutically acceptable salts thereof.

. A still further object of this invention is to provide methods for the treatment of hypertension using new amino acid derivatives or pharmaceutically acceptable salts thereof.

Other objects, features and advantages of this invention will be apparent from the following description of the invention.

The present invention provides new amino acid derivatives represented by formula (I):

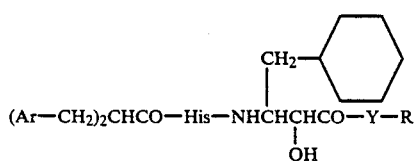

wherein Ar represents a phenyl group, a naphthyl group or pyridyl group which may have a substituent, His represents an L-histidyl group, Y represents —O— or —NH—, R represents a straight- or branched-chain alkyl group, a cycloalkyl group or a halogenated alkyl group, or pharmaceutically acceptable acid addition salts thereof.

DETAILED DESCRIPTION OF THE INVENTION

The amino acid derivatives of formula (I) of this invention and pharmaceutically acceptable salts thereof exhibit an renin inhibitory activity in a human renin-sheep renin substrate system and human plasma renin activity. Furthermore, the amino acid derivatives of this invention are stable against proteolytic enzymes such as pepsin and chymotrypsins.

These findings demonstrate that the amino acid derivatives of formula (I) of this invention exhibit a human renin inhibitory effect when administered orally to mammalia, including humans, and thus are useful for treatment of hypertension, especially renin-associated hypertension.

The amino acid derivatives of formula (I) of this invention can be prepared according to well-known methods. That is, the amino acid derivatives of this invention represented by formula (I):

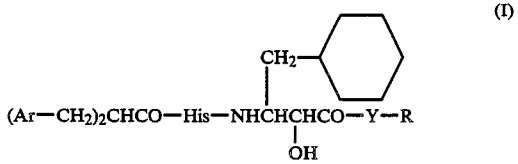

wherein Ar, His, Y and R have the same meanings as defined above, can be prepared by condensing an carboxylic acid compound represented by the general formula:

wherein Ar has the same meaning as defined above, and a compound represented by the general formula:

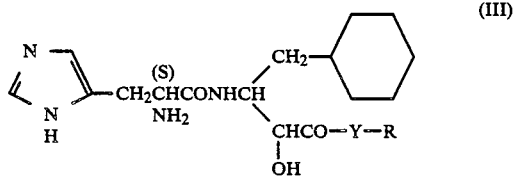

wherein the carbon atom marked with (S) is of S-configuration, Y and R have the same meanings as defined above, in the presence of diphenylphosphoryl azide, or condensing a compound represented by the general formula:

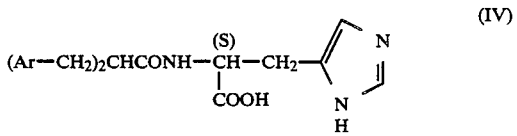

wherein Ar and the carbon atom marked with (S) have the same meanings as defined above, and a compound represented by the general formula:

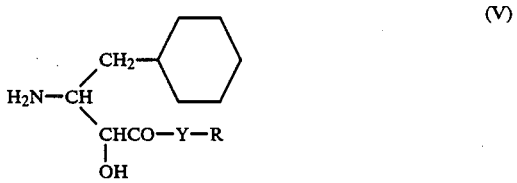

wherein Y and R have the same meanings as defined above, in the presence of diphenylphosphoryl azide.

In this process, the compounds represented by the general formula (II), for example, can be prepared by reacting a compound represented by the general formula:

wherein X represents a halogen atom, Ar has the same meaning as defined above, and ethyl malonate in the presence of a base to obtain a compound represented by the general formula:

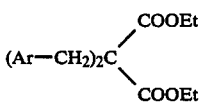

(VII)

wherein Ar has the same meaning as defined above, then removing the ethoxycarbonyl group from the compound of the general formula (VII) with lithium chloride-dimethyl sulfoxide, and hydrolyzing the obtained compound.

The compound of the general formula (IV) can be also prepared by condensing a compound of the general formula (II) and an L-histidine alkyl ester in the presence of diphenylphosphoryl azide, and hydrolyzing the obtained compound.

The compounds represented by the general formula can be prepared by hydrogenating a phenylalanine wherein the amino group is protected by a suitable protective group in the presence of rhodium on alumina powder to obtain a cyclohexylalanine derivative, reducing the obtained compound with a reducing agent such as boran to obtained a cyclohexylalaninol, treating the obtained compound with sulfur trioxide pyridine complex in the presence of triethylamine in benzene to obtain a cyclohexylalaninal derivative, reacting the cyclohexylalaninal derivative and potassium cyanide, hydrolyzing the obtained compound with hydrochloric acid to obtain an amino carboxylic acid compound represented by the formula:

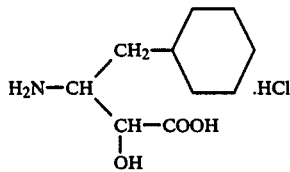

(VIII)

and then esterifying or amidating the compound of the formula (VIII) according to a usual manner.

The compound represented by the general formula (III) can be prepared by condensing a compound of the general formula (V) and L-histidine.

The amino acid compounds represented by the general formula (I) of this invention can be preferably prepared by dissolving a compound of the general formula (II) and a compound of the general formula (III) in an equimolar amount to the compound of the general formula (II), or a compound of the general formula (IV) and a compound of the general formula (V) in an equimolar amount to the compound of the general formula (VI) in N,N-dimethylformamide, adding diphenylphosphoryl azide and triethylamine to the solution, stirring the mixture overnight and then treating the reaction mixture according to a usual manner.

The amino acid derivatives represented by formula (I) of this invention contain three asymmetric carbon atoms including that in the L-histidine moiety, and therefore, various stereoisomers of the amino acid derivatives exist depending upon the configuration of each asymmetric carbon atoms. Although configurations of the asymmetric carbon atoms affect the renin inhibitory activity of the compound represented by formula (I), the configurations of the asymmetric carbon atoms other than that of the L-histidine moiety are not limited in this invention with respect to these isomers.

In the amino acid derivatives represented by formula (I), the configuration of the carbon atom on which the amino group is substituted in the moiety of the compound represented by formula (VIII) is preferably S-configuration, whereas the configuration of the carbon atom on which the hydroxy group is substituted in the above moiety affects the activity, and R-configuration is preferable, but a mixture of S- and R-configuration can be employed.

The optically active starting materials used for preparation of those optically active compounds can be prepared by performing an optical resolution according to a usual manner or using an optically active compound.

The amino acid derivatives represented by formula (I) of this invention can be converted according to conventional methods into pharmaceutically acceptable salts thereof. Examples of such pharmaceutically acceptable salts include pharmaceutically acceptable inorganic or organic acid salts such as a hydrochloric acid salt, a sulfonic acid salt, a p-toluenesulfonic acid salt, an acetic acid salt, a citric acid salt, tartaric acid salt, a succinic acid salt, a fumaric acid salt and the like. These salts have a renin inhibitory effect as high as the corresponding compound having a free amino group and are stable against proteolytic enzymes, and thus they show the desired renin inhibitory effect even by oral administration.

The amino acid derivatives represented by formula (I) of the present invention possess a strong inhibitory effect on human renin, for example, the amino acid derivatives of formula (I) produce a 50% inhibition in human renin-sheep substrate system and in human high renin plasma at $3.3 \times 10^{-6}$ to $9.4 \times 10^{-9}$ and $5.9 \times 10^{-6}$ to $1.3 \times 10^{-7}$ molar concentrations, respectively, and reduce blood pressure of marmosets in a high renin state with a low toxicity, and thus are useful as a therapeutically active agent for treatment of hypertension, especially renin-associated hypertension.

The amino acid derivatives represented by formula (I) and the pharmaceutically acceptable salts thereof of this invention can be administered to mammalia, including humans, by oral, intravenous, intramuscular, or intrarectal administration, and for administration they can be formulated into pharmaceutical compositions together with conventional pharmaceutically acceptable carriers or excipients.

The amino acid derivatives and the pharmaceutically acceptable salts of the formula (I) of this invention can be administered in various dosage forms depending upon the intended therapy. Typical dosage forms which can be used are tablets, pills, powders, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated into sugar-coated tablets, gelatin-coated tablets, film-coated tablets, or tablets coated with two or more layers.

When the pharmaceutical composition is formulated into an injectable preparation, it is preferred that the resulting injectable solution and suspension are sterilized and rendered isotonic with respect to blood. In making the pharmaceutical composition in a form of solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of the amino acid derivatives of this invention may be in the range from about 5 mg to 5,000 mg per adult human by oral administration per day, or from about 1 mg to 1,000 mg per adult human by parenteral administration per day in multiple doses depending upon the type of disease, the severity of condition to be treated, and the like.

This invention is further illustrated in more detail by way of the following Examples, Reference Examples, Text Example. The melting points of the products obtained were uncorrected. The NMR spectra of the products were measured by JEOL's High Resolution NMR Spectrometer Type JNM-GX 270. The Mass spectra of the products were measured by JEOL's Mass Spectrometer Type JMS-DX 300 according to the FAB method. Thin layer chromatography was carried out using Merck's precoated plates silica gel 60 $F_{254}$ and column chromatography was carried out by employing Merck's Kiesel gel 60 (230-400 mesh). Thin layer chromatography was carried out by using a lower layer of a mixture of chloroform, methanol and water in a proportion of 8/3/1 (by volume) (mixture A) and mixture of chloroform and methanol in a proportion of 5/1 (by volume) (mixture B) as eluent, and an $Rf_1$ (mixture A) value and $Rf_2$ (mixture B) value were calculated.

REFERENCE EXAMPLE 1

Bis(2-fluorobenzyl)acetic acid

In 15 ml of dry dimethoxyethane was dissolved 5.2 g of ethyl malonate, and to the solution was added 3.8 g of a 50% sodium hydride (dispersion in an oil) with stirring under ice-cooling. To the mixture was added a solution of 20 ml of dry dimethoxyethane containing 12.3 g of 2-fluorobenzyl bromide. The mixture was stirred for 1 hour at room temperature, and then heated under reflux for 16 hours. The reaction mixture was evaporated under reduced pressure, and to the residue was acidified by an addition of diluted hydrochloric acid. The acidic mixture was extracted with ethyl acetate. The ethyl acetate layer was washed with water, dried over anhydrous magnesium sulfate, and evaporated under reduced pressure. The residue was purified by column chromatography (eluent: benzene) to obtain 8.6 g of ethyl bis(2-fluorobenzyl)malonate as a colorless oil. In a mixture of 20 ml of dimethyl sulfoxide and 1 ml of water was dissolved 8.6 g of ethyl bis(2-fluorobenzyl)malonate, and to the solution was added 4.4 g of lithium chloride. The mixture was heated at 190°-200° C. for 10 hours. After cooling, the reaction mixture was acidified by an addition of diluted hydrochloric acid. The acidic mixture was extracted with ethyl acetate, and the ethyl acetate layer was washed with water, dried over anhydrous magnesium sulfate, and evaporated under reduced pressure. In 50 ml of methanol was dissolved the residue, and to the solution was added 30 ml of a 2N-aqueous sodium hydroxide solution. The mixture was heated under reflux for 1 hour, and the reaction mixture was evaporated under reduced pressure. The residue was dissolved in water, and the solution was extracted with diethyl ether. The aqueous layer was acidified by an addition of hydrochloric acid, and the acidic mixture was extracted with ethyl acetate. The ethyl acetate layer was washed with water, dried over anhydrous magnesium sulfate, and evaporated under reduced pressure. The residue was purified by silica gel column chromatography (eluent: chloroform/methanol=15/1) to obtain 2.85 g of bis(2-fluorobenzyl)acetic acid as a white powder.

melting point: 110°-111° C.
IR (KBr): νco 1700 cm$^{-1}$
NMR (CDCl$_3$) δ: 2.85-3.2(m 5H), 6.9-7.3(m, 8H)

REFERENCE EXAMPLE 2

The following carboxylic acid compounds were prepared in an analogous manner to that described in Reference example 1.

Bis(2-trifluoromethylbenzyl)acetic acid white powder
melting point: 154°-156° C.
IR (KBr): νco 1710 cm$^{-1}$
NMR (CDCl$_3$) δ: 2.9-3.3(m, 5H), 7.2-7.75(m, 8H)

Bis(2-hydroxybenzyl)acetic acid white powder
melting point: 148°-149° C.
IR (KBr): νco 1730 cm$^{-1}$
NMR (CDCl$_3$) δ: 2.85-3.35(m, 5H), 6.46(s, 1H), 6.8-7.3(m, 9H)

Bis(3-fluorobenzyl)acetic acid white powder
melting point: 100°-101.5° C.
IR (KBr): νco 1700 cm$^{-1}$
NMR (CDCl$_3$) δ: 2.65-3.1(m, 5H), 6.8-7.0(m, 6H), 7.15-7.3(m, 2H)

Dibenzylacetic acid white powder
melting point: 87°-89° C.
IR (KBr): νco 1700 cm$^{-1}$
NMR (CDCl$_3$) δ: 2.7-2.85(m, 2H), 2.9-3.05(m, 3H), 7.1-7.3(m, 10H)

Bis(4-methylbenzyl)acetic acid white powder
melting point: 123°-125° C.
(KBr): νco 1700 cm$^{-1}$
NMR (CDCl$_3$) δ: 2.31(s, 6H), 2.7-3.05(m, 5H), 7.07(s, 8H)

Bis(2,6-dimethylbenzyl)acetic acid white powder
melting point: 174°-175° C.
IR (KBr): νco 1700 cm$^1$
NMR (CDCl$_3$) δ: 2.24(s, 12H), 2.8-3.2(m, 5H), 6.95-7.05(m, 6H)

Bis(3-pyridylmethyl)acetic acid white powder
melting point: 161°-162° C.
IR (KBr): νco 1700 cm$^{-1}$
NMR (CDCl$_3$) δ: 2.8-3.15(m, 5H), 7.25-8.55(m, 8H)

Bis(2-bromobenzyl)acetic acid white powder melting point: 142°–143° C.
(KBr): νco 1695 cm$^{-1}$
NMR (CDCl$_3$) δ: 2.95–3.35(m, 5H), 7.05–7.55(m, 8H)

Bis(4-chlorobenzyl)acetic acid white powder
melting point: 108°–111° C.
IR (KBr): νco 1695 cm$^{-1}$
NMR (CDCl$_3$) δ: 2.70–3.00(m, 5H), 7.05–7.40(m, 8H)

Bis(2-chlorobenzyl)acetic acid white powder
melting point: 128°–129° C.
IR (KBr): νco 1690 cm$^{-1}$
NMR (CDCl$_3$) δ: 2.95–3.35(m, 5H), 7.1–7.4(m, 8H)

Bis(3,4-methylenedioxybenzyl)acetic acid white powder
melting point: 182°–184° C.
IR (KBr): νco 1700 cm$^{-1}$
NMR (CDCl$_3$) δ: 2.70–2.95(m, 5H), 5.92(s, 4H), 6.60–6.75(m, 6H)

Bis(1-naphthylmethyl)acetic acid white powder
melting point: 163°–164° C.
IR (KBr): νco 1700 cm$^{-1}$
NMR (CDCl$_3$) δ: 3.25–3.65(m, 5H), 7.2–7.9(m, 14H)

Bis(2,3-dimethylbenzyl)acetic acid white powder
melting point: 184°–186° C.
IR (KBr): νco 1700 cm$^{-1}$
NMR (CDCl$_3$) δ: 2.10(s, 6H), 2.26(s, 6H), 2.8–3.1(m, 5H), 7.01(s, 6H)

Bis(4-fluorobenzyl)acetic acid white powder
melting point: 112°–114° C.
IR (KBr): νco 1690 cm$^{-1}$
NMR (CDCl$_3$) δ: 2.7–3.1(m, 5H), 6.9–7.2(m, 8H)

Bis(3-methylbenzyl)acetic acid viscous pale yellow oil
IR (neat): νco 1700 cm$^{-1}$
NMR (CDCl$_3$) δ: 2.30(s, 6H), 2.7–3.05(m, 5H), 6.95–7.3(m, 8H)

Bis(2-methoxybenzyl)acetic acid white powder
melting point: 85°–86° C.
IR (KBr): νco 1685 cm$^{-1}$
NMR (CDCl$_3$) δ: 2.8–3.0(m, 4H), 3.1–3.2(m, 1H), 3.72(s, 6H), 3.72(s, 6H), 6.75–6.9(m, 4H), 7.1–7.25(m, 4H)

Bis(2-cyanobenzyl)acetic acid white powder
melting point: 113°–115° C.
IR (KBr): νco 1700 cm$^{-1}$, νCN 2230 cm$^{-1}$
NMR (CDCl$_3$) δ: 3.0–3.35(m, 5H), 7.3–7.65(m, 8H)

Bis(2-methylbenzyl)acetic acid white powder
melting point: 94°–95° C.
IR (KBr): νco 1690 cm$^{-1}$
NMR (CDCl$_3$) δ: 2.21(s, 6H), 28–3.1(m, 5H), 7.12(bs, 8H)

Bis(2,3-methylenedioxybenzyl)acetic acid white powder
melting point: 120°–122° C.
IR (KBr): νco 1700 cm$^{-1}$
NMR (CDCl$_3$) δ: 2.75–3.05(m, 4H), 3.15–3.3(m, 1H), 5.85–5.95(m, 4H), 6.6–6.8(m, 6H)

REFERENCE EXAMPLE 3

N-[Bis(2-fluorobenzyl)acetyl]-L-histidine methyl ester

In 30 ml of N,N-dimethylformamide were suspended 1.8 g of bis(2-fluorobenzyl)acetic acid and 1.9 g of L-histidine methyl ester dihydrochloride, and to the suspension were successively added 1.68 ml of diphenylphosphoryl azide and 2.9 ml of triethylamine with stirring under ice-cooling. The mixture was still stirred for 16 hours. The reaction mixture was evaporated under reduced pressure, and to the residue was added a 5% aqueous sodium bicarbonate solution. The mixture was extracted with ethyl acetate, and the ethyl acetate layer was washed with water, dried over anhydrous magnesium sulfate, and evaporated under reduced pressure. The residue was purified by silica gel column chromatography (eluent: chloroform/methanol=1) to obtain 2.0 g of N- bis(2-fluorobenzyl)acetyl-L-histidine methyl ester having an Rf$_1$ value of 0.76 as a white powder.
Rf$_1$: 0.76
IR (KBr): νco 1715, 1630 cm$^{-1}$

REFERENCE EXAMPLE 4

The following ester compounds were prepared in an analogous manner to that described in Reference example 3.

N-[Bis(2-chlorobenzyl)acetyl]-L-histidine methyl ester white powder
Rf$_1$: 0.52
IR (KBr): νco 1730, 1640 cm$^{-1}$

N-[Bis(3,4-methylenedioxybenzyl)acetyl]-L-histidine methyl ester white powder
Rf$_1$: 0.47
IR (KBr): νco 1725, 1640 cm$^{-1}$

N-[Bis(2-methylbenzylacetyl]-L-histidine methyl ester white powder
Rf$_1$: 0.58
IR (KBr): νco 1730, 1640 cm$^{-1}$

N-[Bis(2,3-methylenedioxybenzyl)acetyl]-L-histidine methyl ester white powder
Rf$_1$: 0.57
IR (KBr): νco 1730, 1640 cm$^{-1}$

REFERENCE EXAMPLE 5

(2RS, 3S)-3-Amino-4-cyclohexyl-2-hydroxybutyric acid isopropyl ester hydrochloride In 25 ml of methanol was dissolved 13.25 g of N-(tert-butyloxycarbonyl)-L-phenylalanine, and the solution was hydrogenated over 1.2 g of rhodium on alumina powder under a pressure of 3.5 mg/cm$^2$. After filtration of the catalyst, the filtrate was evaporated to obtain 13.4 g of N-(tert-butyloxycarbonyl)-L-cyclohexylalanine as a white powder.

In 5 ml of dry tetrahydrofuran was dissolved 2.71 g of the N-(tert-butyloxycarbonyl)-L-cyclohexylalanine, and to the solution was added 20 ml of a 1M boran tetrahydrofuran solution under an argon atmosphere while the medium temperature was kept at 5°–8° C. The mixture was still stirred for 3 hours. The reaction mixture was adjusted to a pH of 4 by an addition of a 10% acetic acid methanol solution, and then evaporated under reduced pressure. To the residue was added diethyl ether, and the mixture was successively washed with an aqueous citric acid solution, an aqueous sodium bicarbonate solution and a saturated sodium chloride aqueous solution, dried over an hydrous magnesium sulfate, and evaporated under reduced pressure to obtain 2.42 g of N-(tert-butyloxycarbonyl)-L-cyclohexylalaninol.

A mixture of 2.4 g of N-(tert-butyloxycarbonyl)-L-cyclohexylalaninol, 6.5 ml of dry triethylamine, 3 ml of dry benzene and 6.6 ml of dry dimethyl sulfoxide was cooled to 15° C. (medium temperature), and to the mixture was added dropwise 7.4 g of sulfur trioxide pyridine complex at the medium temperature of 15°–25° C. The mixture was still stirred for 10 minutes. The reaction mixture was poured into water, and the mixture was extracted with ethyl acetate. The ethyl acetate layer was successively washed with a saturated sodium bicarbonate aqueous solution and water, dried over anhydrous magnesium sulfate, and evaporated under reduced pressure to obtain 2.9 g of N-(tert-butyloxycarbonyl)-L-cyclohexylalaninal.

To 2.9 g of the N-(tert-butyloxycarbonyl)-L-cyclohexylalaninal was added a solution of 2.9 g of sodium bisulfete in 20 ml of water under cooling, and the mixture was stirred for 14 hours under cooling. To the reaction mixture were successively added a solution of 1.82 g of potassium cyanide in 5 ml of water and 40 ml of ethyl acetate, and the mixture was stirred for 4 hours at room temperature. The ethyl acetate layer was washed with a saturated sodium chloride aqueous solution, dried over anhydrous magnesium sulfate, and evaporated under reduced pressure. To the residue was added 21 ml of a 23% hydrochloric acid, and the mixture was heated under reflux for 12 hours. The reaction mixture was washed with ether, and the aqueous layer was evaporated under reduced pressure to obtain 2.5 g of (2RS, 3S)-3-amino-4-cyclohexyl-2-hydroxybutyric acid hydrochloride. In 12 ml of isopropanol was dissolved 100 mg of the (2RS, 3S)-3-amino-4-cyclohexyl-2-hexylbutyric acid hydrochloride, and then into the solution was passed hydrogen chloride with stirring under ice-cooling. The mixture was heated under reflux for 2 hours. The mixture was concentrated to dryness under reduced pressure, and the residue was purified by silica gel column chromatography (eluent: chloroform/methanol=15/1) to obtain 108 mg of (2RS, 3S)-3-amino-4-cyclohexyl-2-hydroxybutyric acid isopropyl ester hydrochloride as a white powder.

(KBr): $\nu$co 1735 cm$^{-1}$

NMR (D$_2$O) δ: 0.8–1.8(m, 19H), 3.6–3.8(m, 1H), 4.3–4.6(m, 1H), 5.0–5.2(m, 1H)

REFERENCE EXAMPLE 6

The following ester compounds were prepared in an analogous manner to that described in Reference Example 5.

(2RS, 3S)-Amino-4-cyclohexyl-2-hydroxybutyric acid cyclopentyl ester hydrochloride white powder
IR (KBr): $\nu$co 1730 cm$^{-1}$ NMR (D$_2$O) δ: 0.8–2.0(m, 2H), 3.6–4.0(m, 1H), 4.3–4.7(m, 1H), 5.2–5.4(m, 1H)

(2RS, 3S)-Amino-4-cyclohexyl-2-hydroxybutyric acid cyclohexyl ester hydrochloride colorless viscous oil
IR (KBr): $\nu$co 1730 cm$^{-1}$
NMR (D$_2$O) δ: 0.8–2.0(m, 23H), 3.5–4.0(m, 1H), 4.3–4.7(m, 1H), 4.8–5.0(m, 1H)

(2RS, 3S)-Amino-4-cyclohexyl-2-hydroxybutyric acid 1,3-difluoro-2-propyl ester white powder
IR (KBr): $\nu$co 1735 cm$^{-1}$
NMR (CDCl$_3$) δ: 0.8–2.0(m, 13H), 3.3–3.9(m, 1H), 4.1–5.0(m, 5H), 5.2–5.6(m, 1H)

REFERENCE EXAMPLE 7

(2RS, 3S)-Amino-4-cyclohexyl-2-hydroxybutylylisobutyl amide hydrochloride

In a mixture of 10 ml of water and 10 ml of dioxane were dissolved 1.4 g of (2RS, 3S)-3-amino-4-cyclohexyl-2-hydroxybutyric acid hydrochloride and 1.64 ml of triethylamine, and to the solution was added 3.2 g of di-tert-butyldicarbonate. The mixture was stirred for 16 hours at room temperature. To the reaction mixture was added 20 ml of water, and the mixture was extracted with ether to remove neutral materials. The aqueous layer was acidified by an addition of an aqueous citric acid solution, and then extracted with diethyl ether. The ethereal layer was washed with a saturated sodium chloride aqueous solution, dried over anhydrous magnesium sulfate, and evaporated under reduced pressure to obtain 0.9 g of (2RS, 3S)-3-tert-butyloxycarbonylamino-4-cyclohexyl-2-hydroxybutyric acid as a colorless oil.

In 20 ml of ethyl acetate were dissolved 400 mg of the butyric acid compound obtained, 175 mg of isobutylamine hydrochloride 270 mg of 1-hydroxybenzotriazole and 0.22 ml of triethylamine, and to the solution was added 300 mg of dicyclohexylcarbodiimide with stirring under ice-cooling. The mixture was stirred for 16 hours at room temperature, and then the reaction mixture was cooled in an ice bath. In soluble materials were filtered off, and the filtrate was successively washed with an aqueous citric acid solution, a 5% sodium bicarbonate solution and a saturated sodium chloride aqueous solution, dried over anhydrous magnesium sulfate, and evaporated under reduced pressure to obtain 595 mg of (2RS, 3S)-3-(tert-butyloxycarbonyl)amino-4-cyclohexyl-2-hydroxybutylylisobutyl amide.

In 10 ml of methanol was dissolved 590 mg of the amide compound, and to the solution was added 3.3 ml of a 2N hydrochloric acid. The mixture was heated under reflux for 2 hours at 60° C. The reaction mixture was evaporated under reduced pressure to obtain 254 mg of (2RS, 3S)-3-amino-4-cyclohexyl-2-hydroxybutylylisobutyl amide hydrochloride as a white powder.

(KBr): $\nu$co 1640 cm$^{-1}$
NMR (D$_2$O) δ: 0.8–2.0(m, 20H), 2.9–3.2(m, 2H), 3.5–3.7(m, 1H), 4.2–4.5(m, 1H)

REFERENCE EXAMPLE 8

(2RS, 3S)-3-(Histidyl)amino-4-cyclohexyl-2-hydroxybutyric acid isopropyl ester dihydrochloride In 200 ml of dry chloroform was suspended 10.0 g of L-histidine methyl ester dihydrochloride, and to the suspension were successively added 18.4 ml of triethylamine and 10.2 g of 4-methoxybenzyloxycarbonylazide under cooling. The mixture was stirred for 16 hours at 0° C., and then the reaction mixture was evaporated under reduced pressure. To the residue was added a 5% aqueous sodium bicarbonate solution, and the mixture was extracted with ethyl acetate. The ethyl acetate layer was washed with water, dried over anhydrous magnesium sulfate, and evaporated under reduced pressure. The residue was purified by silica gel flash column chromatography (eluent: chloroform/methanol=10/1) to obtain 11.0 g of N-(4-methoxybenzyloxycarbonyl)-L-histidine methyl ester as a yellow oil. In 112 ml of methanol was dissolved 10.9 g of the ester compound obtained, and to the solution was added 9.9 ml of hydrazine monohydrate. The mixture was stirred for 4 hours at room temperature, and then the reaction mixture was evaporated under reduced pressure. The residue was washed with ethanol and then dried at below 40° C. to obtain 4.9 g of N-(4-methoxybenzyloxycarbonyl)-L-histidine hydrazide as a white powder.

In 15 ml of N,N-dimethylformamide was suspended 1.37 g of the hydrazide compound, and to the suspension were successively added a solution of a 5.95N-dry hydrogen chloride in 2.29 ml of N,N-dimethylformamide and 0.66 ml of isoamyl nitrate with stirring at −20° C. After disappearance of the hydrazide compound, the reaction mixture was cooled to −30° C., and then neutralized by an addition of 1.89 ml of triethylamine to prepare a cold solution of N-(4-methoxybenzyloxycarbonyl)-L-histidine azide. The cold azide solution was added to a solution of 1.00 g of (2RS, 3S)-3-amino-4-cyclohexyl-2-hydroxybutyric acid isopropyl ester in 40 ml of N,N-dimethylformamide with stirring under ice-cooling. The mixture was still stirred for 16 hours, and then the reaction mixture was evaporated under reduced pressure. To the residue was added a 5% aqueous sodium bicarbonate solution, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol=15/1) to obtain 1.70 g of (2RS, 3S)-3-[N-(4-methoxybenzyloxycarbonyl)-L-histidyl]amino-4-cyclohexyl-2-hydroxybutyric acid isopropyl ester as a white powder. In 50 ml of methanol was 1.70 g of the butyric acid isopropyl ester compound, and to the solution were added 10 ml of a 2N hydrochloric acid and 200 mg of a 10% palladium charcoal. The mixture was hydrogenated under an atmospheric pressure. After filtration of the catalyst, the filtrate was evaporated under reduced pressure to obtain 1.36 g of (2RS, 3S)-3-(L-histidyl)amino-4-cyclohexyl-2-hydroxybutyric acid isopropyl ester dihydrochloride as a white powder.

Rf$_1$: 0.40

IR (KBr): $\nu$co 1720, 1670 cm$^{-1}$

REFERENCE EXAMPLE 9

The following compounds were prepared in an analogous manner to that described in Reference Example 8.

(2RS, 3S)-3-[N-(L-Histidyl)]amino-4-cyclohexyl-2-hydroxybutyric acid cyclopentyl ester dihydrochloride white powder Rf$_1$: 0.33

IR (KBr): $\nu$co 1720, 1680 cm$^{-1}$ (2RS, 3S)-3-[N-(L-Histidyl)]amino-4-cyclohexyl-2-hydroxybutyric acid cyclohexyl esterdihydrochloride white powder Rf$_1$: 0.42

IR (KBr): $\nu$co 1720, 1680 cm$^{-1}$

EXAMPLE 1

(2RS, 3S)-3-{N-[Bis(2-fluorobenzyl)acetyl]-L-histidyl}amino-4-cyclohexyl-2-hydroxybutyric acid isopropyl ester (Compound A)

In 5 ml of N,N-dimethylformamide were dissolved 67 mg of bis(2-fluorobenzyl)acetic acid and 100 mg of (2RS, 3S)-3-[N-(L-histidyl)amino]-4-cyclohexyl-2-hydroxybutyric acid isopropyl ester dihydrochloride, and to the solution were successively added 0.06 ml of diphenylphosphoryl azide and 0.1 ml of triethylamine with stirring under ice-cooling. The mixture was still stirred for 16 hours, and the reaction mixture was evaporated under reduced pressure. To the residue was added an aqueous sodium bicarbonate solution, and the mixture was extracted with ethyl acetate. The ethyl acetate layer was washed with a saturated sodium chloride aqueous solution, dried over anhydrous magnesium sulfate, and evaporated under reduced pressure. The residue was purified by preparative silica gel thin layer chromatography (developing solvent: chloroform/methanol=10/1) to 23 mg of (2RS, 3S)-3-{N-[bis(2-fluorobenzyl)acetyl]-L-histidyl}amino-4-cyclohexyl-2-hydroxybutyric acid isopropyl ester having an Rf$_2$ value of 0.59 as a white powder.

melting point: 78°–82° C.

Rf$_1$: 0.62

Rf$_2$: 0.59

MS: MH+, 639

EXAMPLE 2

The following compounds were prepared in an analogous manner to that described in Example 1.

(2RS, 3S)-3-{N-[Bis(2-trifluoromethylbenzyl)acetyl]-L-histidyl}amino-4-cyclohexyl-2-hydroxybutyric acid isopropyl ester (Compound B)

white powder melting point: 77°–81° C.

Rf$_1$: 0.58

Rf$_2$: 0.56

MS MH+, 739

(2RS, 3S)-3-{N-[Bis(2-hydroxybenzyl)acetyl]-L-histidyl}amino-4-cyclohexyl-2-hydroxybutyric acid isopropyl ester (Compound C)

white powder melting point: 110°–114° C.
Rf$_1$: 0.47
Rf$_2$: 0.47
MS: MH+, 635

(2RS, 3S)-3-{N-[Bis(3-fluorobenzyl)acetyl]-L-histidyl}amino-4-cyclohexyl-2-hydroxybutyric acid isopropyl ester (Compound D)

white powder
melting point: 84°–88° C.
Rf$_1$: 0.55
Rf$_2$: 0.55
MS: MH+, 639

(2RS, 3S)-3-[N-(dibenzylacetyl)-L-histidyl}amino-4-cyclohexyl-2-hydroxybutyric acid isopropyl ester (Compound E)

white powder
melting point: 79°–82° C.
Rf$_1$: 0.60
Rf$_2$: 0.51
MS: MH+, 603

(2RS, 3S)-3-{N-[Bis(4-methylbenzyl)acetyl]-L-histidyl}amino-4-cyclohexyl-2-hydroxybutyric acid isopropyl ester (Compound F)

white powder
melting point: 76°–79° C.
Rf$_1$: 0.60
Rf$_2$: 0.52
MS: MH+, 605

(2RS, 3S)-3-{N-[Bis(2,6-dimethylbenzyl)acetyl]-L-histidyl}amino-4-cyclohexyl-2-hydroxybutyric acid isopropyl ester (Compound G)

white powder
melting point: 85°–89° C.
Rf$_1$: 0.61
Rf$_2$: 0.59
MS: MH+, 659

(2RS, 3S)-3-{N-[Bis(3-pyridylmethyl)acetyl]-L-histidyl}amino-4-cyclohexyl-2-hydroxybutyric acid isopropyl ester (Compound H)

white powder
melting point: 78°–81° C.
Rf$_1$: 0.48
Rf$_2$: 0.27
MS: MH+, 631

(2RS, 3S)-3-{N-[Bis(2-bromobenzyl)acetyl]-L-histidyl}amino-4-cyclohexyl-2-hydroxybutyric acid isopropyl ester (Compound I)

white powder
melting point: 78°–80° C.
Rf$_1$: 0.59
Rf$_2$: 0.53
MS: MH+, 759

(2RS, 3S)-3-{N-[Bis(4-chlorobenzyl)acetyl]-L-histidyl}amino-4-cyclohexyl-2-hydroxybutyric acid isopropyl ester (Compound J)

white powder
melting point: 81°–82° C.
Rf$_1$: 0.60
Rf$_2$: 0.53
MS: MH+, 671

(2RS, 3S)-3-[N-(dibenzylacetyl)-L-histidyl]amino-4-cyclohexyl-2-hydroxybutyric acid cyclopentyl ester (Compound K)

white powder
melting point: 78°–80° C.
Rf$_1$: 0.61
Rf$_2$: 0.56
MS: MH+, 629

(2RS, 3S)-3-{N-[Bis(1-naphthylmethyl)acetyl]-L-histidyl}amino-4-cyclohexyl-2-hydroxybutyric acid isopropyl ester (Compound L)

white powder
melting point: 93°–98° C.
Rf$_1$: 0.60
Rf$_2$: 0.60
MS: MH+, 703

(2RS, 3S)-3-{N-[Bis(2,3-dimethylbenzyl)acetyl]-L-histidyl}amino-4-cyclohexyl-2-hydroxybutyric acid isopropyl ester (Compound M)

white powder
melting point: 80°–86° C.
Rf$_1$: 0.61
Rf$_2$: 0.61
MS: MH+, 659

(2RS, 3S)-3-{N-[Bis(2-fluorobenzyl)acetyl]-L-histidyl}amino-4-cyclohexyl-2-hydroxybutyric acid cyclopentyl ester (Compound N)

white powder
melting point: 81°–86° C.
Rf$_1$: 0.59
Rf$_2$: 0.58
MS: MH+, 665

(2RS, 3S)-3-{N-[Bis(4-fouorobenzyl)acetyl]-L-histidyl}amino-4-cyclohexyl-2-hydroxybutyric acid isopropyl ester (Compound O)

white powder
melting point: 85°–88° C.
Rf$_1$: 0.59
Rf$_2$: 0.56
MS: MH+, 639

(2RS, 3S)-3-[N-(benzylacetyl)-L-histidyl}amino-4-cyclohexyl-2-hydroxybutyric acid 1,3-difluoro-2-propyl ester (Compound P)

white powder
melting point: 78°–80° C.
Rf$_1$: 0.59
Rf$_2$: 0.57
MS: MH+, 639

(2RS, 3S)-3-{N-[Bis(3-methylbenzyl)acetyl]-L-histidyl-}amino-4-cyclohexyl-2-hydroxybutyric acid isopropyl ester (Compound Q)

white powder
melting point: 67°-70° C.
Rf$_1$: 0.61
Rf$_2$: 0.59
MS: MH+, 631

(2RS, 3S)-3-{N-[Bis(2-methoxybenzyl)acetyl]-L-histidyl-}amino-4-cyclohexyl-2-hydroxybutyric acid isopropyl ester (Compound R)

white powder
melting point: 71°-74° C.
Rf$_1$: 0.60
Rf$_2$: 0.58
MS: MH+, 663

(2RS, 3)-3-{N-[Bis(2-fluorobenzyl)acetyl]-L-histidyl}amino-4-cyclohexyl ester (Compound S)

white powder
melting point: 78°-82° C.
Rf$_1$: 0.58
Rf$_2$: 0.49
MS: MH+, 679

(2RS, 3S)-3-{N-[Bis(2-cyanobenzyl)acetyl]-L-histidyl}amino-4-cyclohexyl-2-hydroxybutyric acid isopropyl ester (Compound T)

white powder
melting point: 85°-89° C.
Rf$_1$: 0.61
Rf$_2$: 0.60
MS: MH+, 653

EXAMPLE 3

(2RS, 3S)-3-{N-[Bis(2-fluorobenzylacetyl]-L-histidyl}amino-4-cyclohexyl-2-hydroxybutyric acid isopropyl ester (Compound A)

In 10 ml of methanol was dissolved 1.0 g of N-[2-(1-naphthylmethyl)-3-(morpholinocarbonyl)propionyl]-L-histidine methyl ester, and to the solution was added 2.3 ml of a 1N-aqueous sodium hydroxide solution with stirring under ice-cooling. The mixture was stirred for 16 hours at room temperature. The reaction mixture was evaporated under reduced pressure. In 15 ml of N,N-dimethylformamide were dissolved the residue and 500 mg of (2RS, 3S)-3-amino-4-cyclohexyl-2-hydroxybutyric acid isopropyl ester hydrochloride, and to the solution were successively added 0.6 ml of diphenylphosphoryl azide and 0.38 ml of triethylamine with stirring under ice-cooling The mixture was stirred for 50 hours at room temperature, and then the reaction mixture was evaporated under reduced pressure. To the residue was added a 5% aqueous sodium bicarbonate solution, and the mixture was extracted with ethyl acetate. The ethyl acetate layer was washed with a saturated sodium chloride aqueous solution, dried over anhydrous magnesium sulfate, and evaporated under reduced pressure. The residue was purified by silica gel flash column chromatography (eluent: chloroform/methanol=15/1) to obtain 650 mg of (2RS, 3S)-3-{N-[Bis(2-fluorobenzylacetyl]-L-histidyl}amino-4-cyclohexyl-2-hydroxybutyric acid isopropyl ester having an Rf$_2$ value of 0.59 as a white powder.
melting point: 78°-82° C.
Rf$_1$: 0.62
Rf$_2$: 0.59
MS: MH+, 639

EXAMPLE 4

The following compounds were prepared in an analogous manner to that described in Example 4.

(2RS, 3S)-3-{N-[Bis(2-chlorobenzyl)acetyl]-L-histidyl-}amino-4-cyclohexyl-2-hydroxybutyric acid butyric acid isopropyl ester (Compound U)

white powder
melting point: 81°-82° C.
Rf$_1$: 0.60
Rf$_2$: 0.53
MS: MH+, 671

(2RS, 3S)-3-{N-[Bis(3,4-methylenedioxybenzyl)acetyl]-L-histidyl}amino-4-cyclohexyl-2-hydroxybutyric acid isopropyl ester (Compound V)

white powder
melting point: 86°-89° C.
Rf$_1$: 0.62
Rf$_2$: 0.52
MS: MH+, 691

(2RS, 3S)-3-{N-[Bis(2-methylbenzyl)-acetyl]-L-histidyl-}amino-4-cyclohexyl-2-hydroxybutyric acid isopropyl ester (Compound W)

white powder
melting point: 85°-92° C.
Rf$_1$: 0.59
Rf$_2$: 0.50
MS: MH+, 631

(2RS, 3S)-3-{N-[Bis(2,3-methylenedioxybenzyl)acetyl]-L-histidyl}amino-4-cyclohexyl-2-hydroxybutyric acid isopropyl ester (Compound X)

white powder
melting point: 79°-84° C.
Rf$_1$: 0.60
Rf$_2$: 0.49
MS: MH+, 691

(2RS, 3S)-3-{N-[Bis(2,3-methylenedioxybenzyl)acetyl]-L-histidyl}amino-4-cyclohexyl-2-hydroxybutyric acid isobutyl amide (Compound Y)

white powder
melting point: 94°-97° C.
Rf$_1$: 0.59
Rf$_2$: 0.47
MS: MH+, 704

TEST EXAMPLE 1

Inhibitory effect on human renin-sheep renin substrate reaction system in vitro

To a mixture of 200 μl of a 125 mM pyrophosphate buffer (pH 7.4) containing 5 mM EDTA.2Na and a 0.1% neomycin sulfate, 25 μl of a 20 mM L-phenylalanyl-L-alanyl-L-proline as an angiotensin converting enzyme inhibitor 50 μl of semipurified sheep renin substrate (2000 ng angiotensin I:eq./ml), 50 μl of dimethyl sulfoxide solution of an amino acid derivative of the present invention and 150 μl of deionized water was added 25 μl of purified human renin (20–30 ng angiotensin I/ml/hr). The mixture was incubated for 15 minutes on a water bath at 37° C., and the reaction mixture was allowed to stand for 5 minutes on a water bath at 100° C. to stop the reaction. After cooling, 200 μl of the solution was taken up and the amount of angiotensin I produced by the addition of renin was determined by radioimmunoassay using renin riabead kit (DAINABOT).

The inhibitory effect was calculated by the following equation.

As a control, the same procedure as above was carried out by using 50 μl of dimethyl sulfoxide alone in place of the 50 μl of dimethyl sulfoxide solution containing an amino acid compound of the present invention.

$$\text{Inhibition (\%)} = \frac{\text{Amount of angiotensin I in control} - \text{Amount of angiotensin I in a mixture containing a compound of the present invention}}{\text{Amount of angiotensin I in control}} \times 100$$

The molar concentration producing a 50% inhibition ($IC_{50}$) was calculated from the inhibition values obtained, and the results are shown below.

| Compounds | $IC_{50}$ molar concentration |
|---|---|
| Compound A | $9.4 \times 10^{-9}$ M |
| Compound B | $1.2 \times 10^{-7}$ M |
| Compound C | $1.8 \times 10^{-7}$ M |
| Compound D | $1.8 \times 10^{-8}$ M |
| Compound E | $5.2 \times 10^{-8}$ M |
| Compound F | $2.0 \times 10^{-7}$ M |
| Compound G | $9.0 \times 10^{-7}$ M |
| Compound H | $3.3 \times 10^{-6}$ M |
| Compound I | $1.8 \times 10^{-8}$ M |
| Compound J | $4.7 \times 10^{-7}$ M |
| Compound K | $1.8 \times 10^{-8}$ M |
| Compound L | $4.9 \times 10^{-8}$ M |
| Compound M | $7.7 \times 10^{-8}$ M |
| Compound N | $2.9 \times 10^{-8}$ M |
| Compound O | $6.8 \times 10^{-8}$ M |
| Compound P | $1.9 \times 10^{-8}$ M |
| Compound Q | $6.0 \times 10^{-8}$ M |
| Compound R | $1.7 \times 10^{-7}$ M |
| Compound S | $6.2 \times 10^{-8}$ M |
| Compound T | $1.9 \times 10^{-7}$ M |
| Compound U | $6.3 \times 10^{-8}$ M |
| Compound V | $9.1 \times 10^{-7}$ M |
| Compound W | $5.8 \times 10^{-8}$ M |
| Compound X | $3.3 \times 10^{-7}$ M |
| Compound Y | $1.8 \times 10^{-6}$ M |

TEST EXAMPLE 2

Renin Inhibitory Effect in a Human High Renin Plasma

A mixture of 350 μl of a 0.5M phosphate buffer (pH 7.0) containing 14 nM EDTA.2Na and a 0.3% neomycin sulfate, 50 μl of a 20 mM L-phenylalanyl-L-alanyl-L-proline as an angiotensin converting enzyme inhibitor and 100 μl of dimethyl sulfoxide solution containing an amino acid derivative of the present invention was added to 500 μl of human high renin plasma. Two hundred μl of the mixture was placed on an ice bath, at 4° C., and remaining mixture (800 μl) was incubated for 60 minutes at 37° C. on a water bath. Two hundred μl of the incubated remaining mixture was chilled immediately on an ice bath, and the amount (A) of angiotensin I produced was determined by radioimmunoassay using renin riabead kit (DAINABOT).

The amount (B) of angiotensin I in the mixture placed on an ice bath at 4° C. was also determined by radioimmunoassay.

As a control, the same procedure as above was carried out by using 100 μl of dimethyl sulfoxide alone in place of 100 μl of dimethyl sulfoxide solution containing an amino acid compound of the present invention.

The net amount was estimated as the difference between A and B.

The inhibitory effect was calculated by the following equation.

$$\text{Inhibition (\%)} = \frac{\text{Amount of angiotensin I in control} - \text{Amount of angiotensin I in a mixture containing a compound of the present invention}}{\text{Amount of angiotensin I in control}} \times 100$$

The molar concentration producing a 50% inhibition ($IC_{50}$) was calculated from the inhibition values obtained, and the results are shown below.

| Compounds | $IC_{50}$ molar concentration |
|---|---|
| Compound A | $1.3 \times 10^{-7}$ M |
| Compound B | $1.2 \times 10^{-6}$ M |
| Compound C | $4.0 \times 10^{-7}$ M |
| Compound D | $2.5 \times 10^{-7}$ M |
| Compound E | $2.6 \times 10^{-7}$ M |
| Compound F | $1.7 \times 10^{-6}$ M |
| Compound G | $3.3 \times 10^{-6}$ M |
| Compound H | $6.4 \times 10^{-7}$ M |
| Compound I | $4.3 \times 10^{-7}$ M |
| Compound J | $5.9 \times 10^{-6}$ M |
| Compound K | $2.8 \times 10^{-7}$ M |
| Compound L | $4.3 \times 10^{-7}$ M |
| Compound M | $8.6 \times 10^{-7}$ M |
| Compound N | $2.3 \times 10^{-7}$ M |
| Compound O | $1.2 \times 10^{-6}$ M |
| Compound P | $1.3 \times 10^{-7}$ M |
| Compound Q | $5.4 \times 10^{-7}$ M |
| Compound R | $3.6 \times 10^{-7}$ M |
| Compound S | $4.3 \times 10^{-7}$ M |
| Compound T | $2.8 \times 10^{-7}$ M |
| Compound U | $4.3 \times 10^{-7}$ M |
| Compound V | $2.6 \times 10^{-6}$ M |
| Compound W | $2.8 \times 10^{-7}$ M |
| Compound X | $6.4 \times 10^{-7}$ M |
| Compound Y | $3.4 \times 10^{-6}$ M |

TEST EXAMPLE 3

Renin Inhibitory Effect in Plasma on Common Marmoset

The experiment was carried out by using common marmoset as described in K. G. Hofbauer et al., *CLINICAL AND EXPERIMENTAL HYPERTENSION*, Vol. A5, Nos. 7 & 8 (1983), pages 1237–1247.

Furosemide was administered orally three times to common marmoset having a lower salt diet at 15 mg per kilogram per day every other day to create a high renin state. The experiment was carried out on the third day after the last furosemide dose.

Measurement

Three conscious male marmosets weighing 310–460 g were placed into small restraining chair, and by using a catheter into the femoral artery, blood collecting was carried out at intervals of 60, 180 and 300 minutes.

Collected blood samples were centrifuged at 1200×g for 15 minutes at 4° C. Two hundred μl of the plasma was taken up and incubated for 60 minutes at 37° C., and the plasma renin activity was measured by radioimmunoassay using renin riabead kit (DAINABOT).

Compound A of this invention was dissolved in dilute hydrochloric acid, and administered orally at single dose of 30 mg/kg using catheter.

The results obtained are shown below.

|  | PRA ng angiotensin I/ml/hr |
|---|---|
| Control | 43.16 |
| 60 minutes after administration | 30.35 |
| 180 minutes after administration | 18.89 |
| 300 minutes after administration | 22.93 |

TEST EXAMPLE 4

Hypotensive Effect in Marmoset

The experiment was carried out by using common marmoset as described in K. G. Hofbauer et al., *Clinical and Experimental Hypertension*, Vol. A5, Nos. 7 & 8 pages 1237–1247.

Furosemide was administered orally three times to common marmoset at 15 mg per kilogram per day every other day to create a high renin state. Blood pressure of conscious marmoset was measured on the third day after the last furosemide dose.

Measurement of Blood Pressure

A conscious male marmoset weighing 340 g was placed into small restraining chair. Blood pressure was measured on the tail cuff method using pretismograph. Compound A of this invention was dissolved in dilute hydrochloric acid, and administered orally at 30 mg/kg by using a catheter. The result obtained is shown below.

| Time after administration (hours) | Blood pressure (mmHg) |
|---|---|
| Control | 99.7 |
| 0.5 | 94.7 |
| 1 | 86.2 |
| 2 | 89.7 |
| 3 | 86.2 |
| 5 | 85.7 |

What is claimed is:

1. An amino acid derivative represented by formula (I):

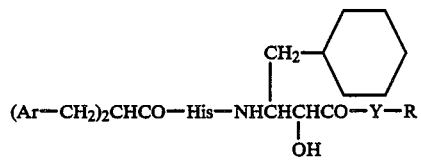

wherein Ar represents a phenyl group, a naphthyl group or pyridyl group which may have a substituent, His represents an L-histidyl group, Y represents —O— or —NH—, R represents a straight- or branched-chain alkyl group, a cycloalkyl group or a halogenated alkyl group, and a pharmaceutically acceptable acid addition salt thereof.

2. An amino acid compound as claimed in claim 1, represented by the general formula:

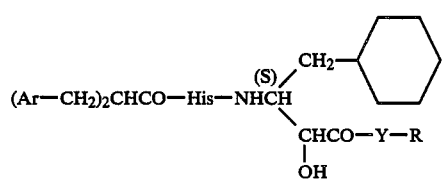

wherein the carbon atom marked with (S) is of S-configuration, Ar, His, Y and R have the same meanings as defined above, or a pharmaceutically acceptable salt thereof, and a pharmaceutically acceptable acid addition salt thereof.

3. An amino acid compound as claimed in claim 2, represented by the general formula:

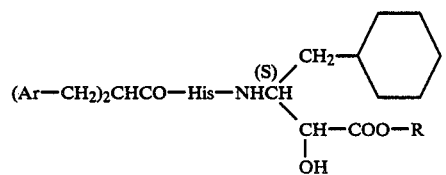

wherein Ar, His, R and the carbon atom marked with (S) have the same meanings as defined above, and a pharmaceutically acceptable acid addition salt thereof.

4. An amino acid compound as claimed in claim 2, represented by the general formula:

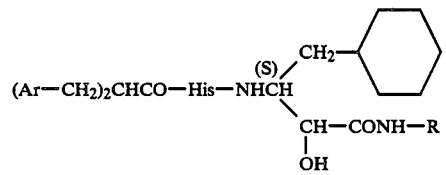

wherein Ar, His, R and the carbon atom marked with (S) have the same meanings as defined above, and a pharmaceutically acceptable acid addition salt thereof.

* * * * *